(12) United States Patent
Stallmann et al.

(10) Patent No.: US 11,079,349 B2
(45) Date of Patent: Aug. 3, 2021

(54) ELECTRICAL MEASURING ASSEMBLY

(71) Applicant: Testo SE & Co. KGaA, Lenzkirch (DE)

(72) Inventors: Siegfried Stallmann, Bonndorf (DE); Oliver Wiech, Donaueschingen (DE)

(73) Assignee: Testo SE & Co. KGaA, Lenzkirch (DE)

( * ) Notice: Subject to any disclaimer, the term of this patent is extended or adjusted under 35 U.S.C. 154(b) by 94 days.

(21) Appl. No.: 16/605,381

(22) PCT Filed: Mar. 19, 2018

(86) PCT No.: PCT/EP2018/056867
§ 371 (c)(1),
(2) Date: Oct. 15, 2019

(87) PCT Pub. No.: WO2018/197108
PCT Pub. Date: Nov. 1, 2018

(65) Prior Publication Data
US 2021/0123880 A1   Apr. 29, 2021

(30) Foreign Application Priority Data

Apr. 28, 2017 (DE) .................... 10 2017 109 227.7

(51) Int. Cl.
*G01N 27/22* (2006.01)
*A47J 36/02* (2006.01)
*G01N 33/03* (2006.01)

(52) U.S. Cl.
CPC .......... *G01N 27/226* (2013.01); *A47J 36/02* (2013.01); *G01N 27/221* (2013.01); *G01N 33/03* (2013.01)

(58) Field of Classification Search
CPC ........ A47J 36/02; G01N 33/03; G01N 27/221
See application file for complete search history.

(56) References Cited

U.S. PATENT DOCUMENTS

| | | | |
|---|---|---|---|
| 6,586,949 B1 | 7/2003 | Sargent et al. | |
| 7,504,836 B2 | 3/2009 | Chambon et al. | |
| 2008/0262740 A1* | 10/2008 | Potter | C12Q 1/006 |
| | | | 702/19 |
| 2010/0156443 A1 | 6/2010 | Nakamura et al. | |
| 2013/0036916 A1 | 2/2013 | Burkett et al. | |
| 2013/0306493 A1* | 11/2013 | Chatelier | G01N 27/413 |
| | | | 205/782 |

(Continued)

FOREIGN PATENT DOCUMENTS

| | | |
|---|---|---|
| DE | 19708067 | 9/1998 |
| DE | 60312389 | 11/2007 |

(Continued)

*Primary Examiner* — Alvaro E Fortich
(74) *Attorney, Agent, or Firm* — Volpe Koenig

(57) ABSTRACT

In an electrical measuring assembly (1), in which an inner electrode (2) and an outer electrode (3), which form a measuring chamber (4) therebetween for a capacitive examination of a liquid flowing past, are formed from a food-safe stainless steel, the inner electrode (2) is supported at the axial ends (6, 7) thereof on the outer electrode (3) by insulating elements (10, 11), which are produced from a ceramic material or plastic material that can be machined and/or that has a permittivity that is temperature-independent in a working range and/or that is free of pores and/or does not absorb water.

19 Claims, 3 Drawing Sheets

(56) References Cited

U.S. PATENT DOCUMENTS

| | | | |
|---|---|---|---|
| 2014/0134655 A1* | 5/2014 | Elder | G01N 27/3274 |
| | | | 435/14 |
| 2015/0108142 A1 | 4/2015 | Chan | |
| 2015/0285777 A1* | 10/2015 | Baumann | G01N 27/24 |
| | | | 73/64.56 |

FOREIGN PATENT DOCUMENTS

| | | |
|---|---|---|
| DE | 102015225502 | 6/2016 |
| EP | 2937692 | 10/2015 |
| EP | 2957903 | 12/2015 |
| GB | 2423463 | 8/2006 |

\* cited by examiner

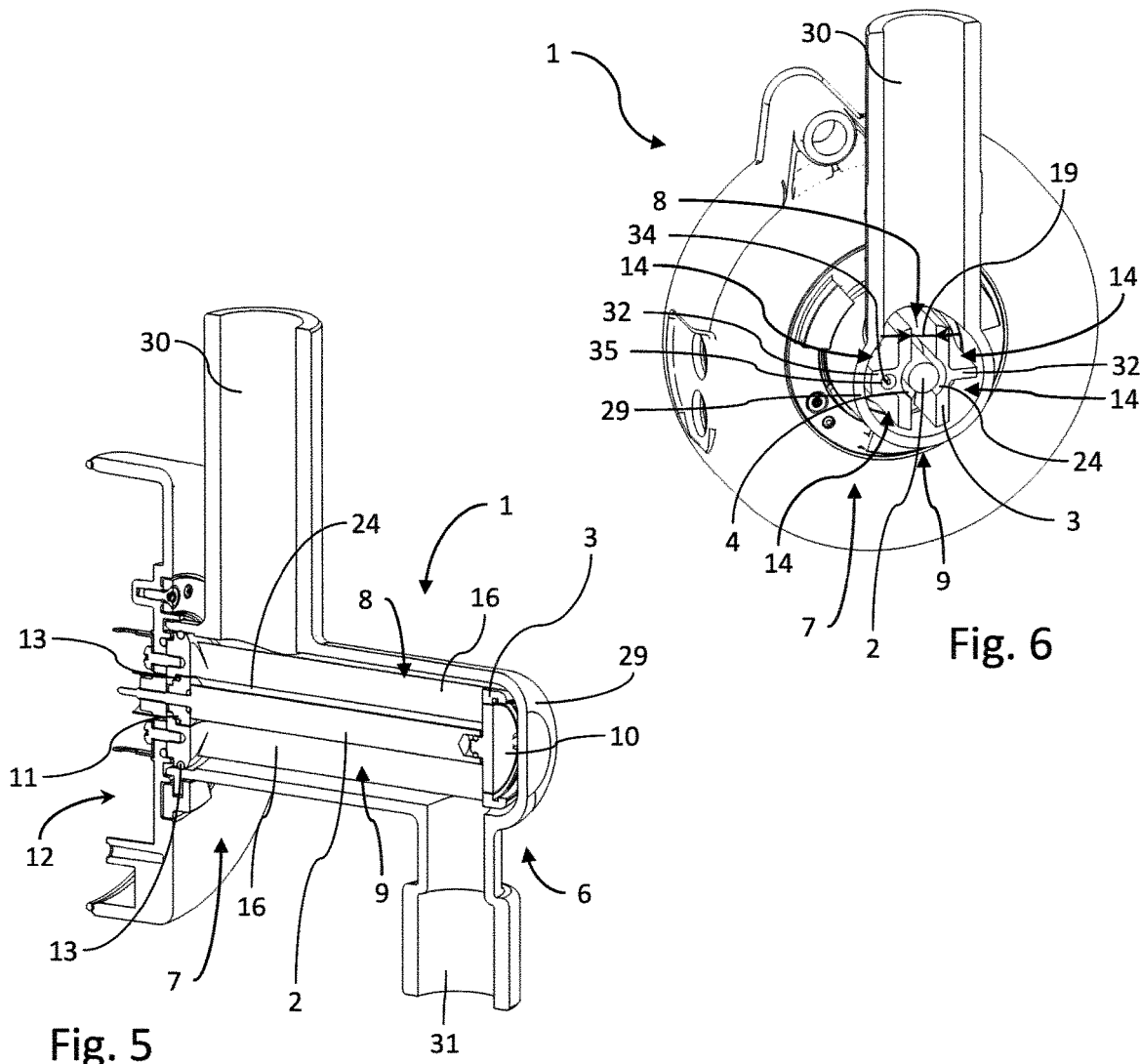
Fig. 6
Fig. 5
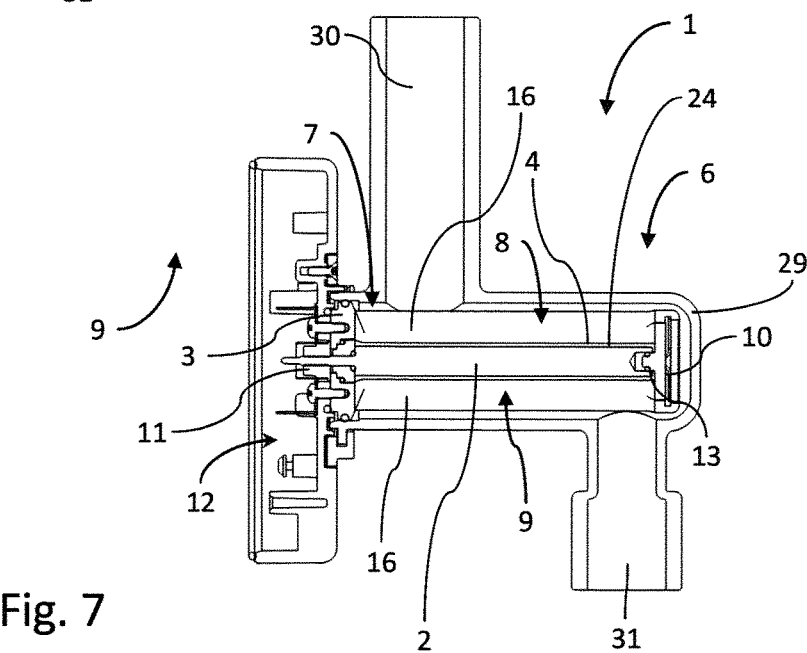
Fig. 7

ELECTRICAL MEASURING ASSEMBLY

BACKGROUND

The invention relates to an electrical measuring assembly for the capacitive measurement of a liquid, having an inner electrode which is arranged concentrically to an outer electrode which encloses the latter, such that a measuring chamber is constituted between the inner electrode and the outer electrode, wherein the inner electrode is secured to the outer electrode at axial ends of the measuring chamber, and wherein an inlet opening to the measuring chamber and a discharge opening from the measuring chamber are constituted in the outer electrode.

Electrical measuring assemblies of this type are known, and are employed, for example, for the monitoring of the quality of a frying oil or frying fat in a frying device or frying installation. The property is exploited whereby the dielectric constant of frying oil or frying fat changes, the longer the frying oil or frying fat is in use. The dielectric constant thus influences the capacitance of a capacitor constituted by the outer electrode and the inner electrode, which capacitance can be determined electrically and/or electronically.

The mutually concentric arrangement of outer electrode and inner electrode has an advantage over the likewise known planar electrode arrangements, and can be characterized, for example, in that, externally to the measuring chamber or the outer electrode—with the exception of marginal effects, for example at ends of the measuring chamber in relation to a longitudinal axis of the coaxial arrangement—virtually no stray field is present, which might impair sensitive capacitive measurement.

SUMMARY

The object of the invention is the construction of an electrical measuring assembly having improved service properties.

For the fulfilment of this object, an electrical measuring assembly having one or more features of the invention is provided. In particular, for the fulfilment of the above-mentioned object in an electrical measuring assembly of the above-mentioned type, it is provided according to the invention that the outer electrode and the inner electrode are formed of stainless steel, and that the inner electrode is retained at the axial ends by a respective insulating element, wherein the insulating elements are formed of a food-safe material. Preferably, the material is a glass ceramic or a plastic. In relation to the known measuring assemblies, the invention thus provides a measuring assembly with a simplified selection of materials, such that the terms of food safety regulations can be fulfilled more easily. In particular, the invention recognizes that the employment of glass ceramic for insulating elements is firstly associated with good electrical insulation properties and that, secondly, any impairment or contamination of the liquid flowing past, for example frying oil or frying fat, is avoidable, or can even be excluded altogether. The service properties of the measuring assembly can be improved accordingly. It is particularly favorable if the material of the insulating elements incorporates at least one of the features a) to d), preferably a plurality of the features a) to d), from the following group:

The insulating elements are a) comprised of a material, the permittivity of which, over the temperature range from 20° C. to 200° C., varies by a maximum of 30%, preferably by a maximum of 10%, particularly preferably by a maximum of 5%, and more particularly preferably by a maximum of 2%, or is virtually constant, and/or b) comprised of a pore-free material, and/or c) comprised of a material which absorbs no water, and/or d) comprised of a chip-machineable material.

The use of chip-machineable glass ceramics has the advantage that small manufacturing tolerances can be observed such that, with no great complexity, for example by means of a grinding post-treatment, adjustment and a defined orientation of the inner electrode in the outer electrode can be achieved. This facilitates in-factory calibration. Service properties are improved accordingly. The insulating elements are preferably machine-turned. The ability to absorb water has proved to have an adverse effect upon the accurate determination of capacitance. The latter can be achieved, for example, by means of a pore-free material. Pore-free materials can also possess good properties with respect to machine turning.

The use of glass ceramic has the further advantage that a good temporal consistency of the electrical properties of the insulating elements can be achieved. This advantageously permits the obviation of recurrent calibrations of the measuring assembly. This also improves service properties.

In one configuration, it can be provided that the measuring chamber encloses the inner electrode in a circumferential direction, or is restricted to a closed circumferential section or a plurality of closed circumferential sections.

In one configuration of the invention, it can be provided that the stainless steel is food-safe. Additional coatings, for example for the food-safe conveyance of a frying oil or frying fat which is to be re-used in food preparation, can be omitted accordingly. The use of stainless steel with the material number 1.4404, or AISI 316L, is particularly favorable. This can be achieved, for example, by the employment of a stainless steel with the generic name X2CrNiMo17-12-2.

In one configuration of the invention, it can be provided that the insulating elements comprise a glass matrix with glimmer crystals. It has been established that selecting a material of this type is particularly conducive to the prevention of any penetration of liquids into the insulating element, which might result in a change in the dielectric properties over time. Compact insulating elements can thus be provided, which can be produced by chip-machining, in particular by turning, for example from a bar material.

The use of a borosilicate glass matrix has proved to be particularly favorable. Insulating elements with 55% fluorophlogopite glimmer and/or 45% borosilicate glass have particularly good mechanical machining properties.

Chip-machinable glass ceramics are supplied, for example, by the firm Schroder Spezialglas GmbH, Buchenweg 20, 25479 Ellerau, under the trade name "MACOR".

These materials can be characterized, for example, by a chemical composition comprising 46% silicon oxide, 17% magnesium oxide, 16% aluminum oxide, 10% potassium oxide, 7% boron oxide, and 4% fluorine.

In one configuration of the invention, it can be provided that the insulating elements are configured to a pore-free design. This is achievable, for example, by means of the insulating elements described having a glass matrix with glimmer crystals. The absence of pores is such that the active material of the insulating elements is particularly compact, such that any ingress of water during the use of the measuring assembly can be prevented. This enhances the temporal stability of the measuring assembly and eliminates complex subsequent calibration steps.

In one configuration of the invention, it can be provided that the insulating elements are produced as turned parts. Production in the form of a turned part has the advantage that the insulating elements can be incorporated into cylindrical or circular assemblies with no further processing. By the option for machine turning, the diameters can be accurately matched to one another such that a specific orientation of the inner electrode in relation to the outer electrode can be achieved in a simple manner. This is necessary for the most accurate possible mathematical modelling of the capacitance of the capacitor constituted between the inner electrode and the outer electrode. This mathematical modelling has the advantage that the detection of temperature influences on the capacitance of the capacitor, for example associated with thermal expansion, can also be represented in a simple manner.

Particularly for application in the food industry, it is advantageous if at least one seal of a food-safe sealing material is arranged between the inner electrode and at least one of the insulating elements. Alternatively or additionally, it can be provided that at least one seal of a food-safe sealing material is arranged between at least one of the insulating elements, for example the above-mentioned at least one insulating element, and the outer electrode. The employment of food-safe materials for sealing has the advantage that no further protective measures are required for the protection of the liquid conveyed against impurities.

In general, it is advantageous if the measuring assembly is comprised exclusively of the materials stainless steel and glass ceramic, in particular those respectively described heretofore, together with a food-safe sealing material, where applicable.

In one configuration of the invention, it can be provided that the outer electrode, on the outer side, incorporates at least one material retraction. This is advantageous in that, with unchanged maximum external dimensions of the outer electrode and an unchanged design of the measuring chamber, a reduction of the material employed for the outer electrode can be achieved. This reduction of material employed in particular results in a reduction of the thermal capacity of the outer electrode. The outer electrode can thus more rapidly assimilate temperature variations in the liquid conveyed. In particular if the outer electrode is temperature-monitored, for example by means of a temperature sensor which is arranged in a recess in the outer electrode, a more accurate consideration of the temperature response of the measuring assembly can be achieved. It is particularly advantageous if the material retraction is configured adjacent to the inlet opening and/or to the discharge opening. Advantageously, the inlet opening and/or the discharge opening can assume the maximum external dimensions of the outer electrode such that, in each case, a channel for the liquid with a maximum possible channel length can be constituted. A channel of this type constitutes effective external shielding, by means of which a stray field from the measuring chamber can be reduced, or even virtually entirely eliminated.

Alternatively or additionally, it can be provided that the material retraction is configured over a length of the measuring chamber. This permits the provision of an outer electrode having the most consistent possible basic cross-sectional shape along the length of the measuring chamber, i.e., for example, along a longitudinal axis of the coaxial arrangement of the outer electrode and the inner electrode.

For the fulfilment of the above-mentioned object according to the invention, a configuration having a potentially independently inventive quality, alternatively or additionally, is provided. In particular, according to the invention, in an electrical measuring assembly of the above-mentioned type, alternatively or additionally to that described heretofore, it is thus proposed that the inlet opening and the discharge opening are respectively configured as radially open, and that an internal clearance of the inlet opening and the discharge opening, transversely to the longitudinal direction, is smaller than an internal diameter of the measuring chamber. Accordingly, inlet or discharge openings with comparatively small opening widths, dictated by the internal clearance, are configured, through which only a limited stray field of the capacitor, which is constituted by the outer electrode and the inner electrode, reaches the exterior. Preferably, the internal clearance is even smaller than a diameter of the inner electrode. Accordingly, the openings, in comparison with a geometry of the measuring chamber, can be configured to smaller dimensions. A component of the electric field in the measuring chamber, which can reach the exterior through the openings, can thus be restricted to a particularly small proportion. The execution of capacitance measurement is thus practically uninfluenced by variations externally to the outer electrode. The service properties of the measuring assembly can be improved accordingly. A Faraday cage can thus be constituted.

The invention thus achieves a throughflow in the measuring chamber, the velocity vector of which incorporates a non-vanishing radial or—in relation to a longitudinal extension or an axis of the coaxial arrangement—transverse component, dictated by the radial orientation of the inlet opening and the discharge opening, whereas the employment of chip-machinable glass ceramics permits a simple and specific orientation of the inner electrode in relation to a position of the longitudinal slots. This has proved to be a particularly effective means for the prevention of any fouling of the measuring chamber by particles or solid constituents in the liquid. The necessity for the excessively frequent dismantling of the measuring assembly for cleaning purposes can be avoided accordingly. This has proved to be advantageous, in that sensitive capacitive measurement, on the grounds of its extreme dependence upon the geometry of the measuring assembly, dictates the recalibration of said measuring assembly after each dismantling.

A combination of these features according to the invention with the previously described solution, or with the advantageous configurations thereof, is particularly advantageous. Thus, for example by the constitution of the outer electrode of (solid) stainless steel, a particularly effective shielding effect on the inlet opening and the discharge opening is achieved, whereas the employment of chip-machined glass ceramics permits a simple and specific orientation of the inner electrode in relation to a position of the longitudinal slots.

In one configuration of the invention, it can be provided that the inlet opening and the discharge opening is/are respectively configured as a radially open longitudinal slot, respectively oriented in a longitudinal direction of the outer electrode. It can be provided that the internal clearance corresponds to a slot width.

Alternatively, it can be provided that the inlet opening and/or the discharge opening is/are configured as at least one bore. This can be produced in a particularly simple manner. A respective sequence of bores, which can extend in a longitudinal direction, can also be constituted. A row of holes can thus be configured, in the interests of the formation of the most uniform possible cylindrical capacitor, and additionally for the minimization of costs (by drilling rather than milling).

In one configuration of the invention, it can be provided that the inlet opening extends over at least half the length of the measuring chamber. The measuring chamber can therefore be flushed over a large part of its extension. The settlement of food residues and the like can thus be effectively prevented. Preferably, the discharge opening extends over at least three quarters of the length, or even the entire length, of the measuring chamber. Regions in which the liquid remains stationary and is not flushed away, for example in undercuts, can also be avoided accordingly. Stationary liquid components of this type can corrupt the result of measurement, in the event of a change in the (remaining) liquid flux. Dead spaces, in which air bubbles might collect in the measuring chamber, can thus be prevented.

Alternatively or additionally, it can be provided that the discharge opening extends over at least half the length of the measuring chamber. This is advantageous, in that an extensive evacuation of the measuring chamber can be achieved. Deposits, which might corrupt the result of measurement, can be prevented accordingly. Preferably, the discharge opening extends over at least three quarters of the length, or even the entire length, of the measuring chamber. This is particularly conducive to a residue-free, or at least to a low-residue, evacuation of the measuring chamber.

In general, it can be observed that, where the inlet opening and the discharge opening are configured to the maximum possible length, the more conducive this will be to the avoidance of residues in the measuring chamber. In this case, the length of the measuring chamber constitutes a natural boundary. At the same time, it is advantageous if the inlet opening and the discharge opening have the smallest possible internal clearance, in particular a particularly narrow slot width, in order to minimize the generation of stray fields, insofar as possible.

In one configuration of the invention, it can be provided that the inlet opening and the discharge opening are arranged on mutually opposing sides of the outer electrode. It can thus be achieved, for example, that the inlet opening and the discharge opening are arranged in mutual diametric opposition—in relation to a longitudinal axis of the coaxial arrangement—and that the inlet opening and the discharge opening are mutually aligned. It is particularly advantageous if the inner electrode is arranged between the inlet opening and the discharge opening. This is advantageous that flux of fluid is compelled to flow around the inner electrode. This assists in the prevention of the above-mentioned deposits and stationary components of the liquid.

In one configuration of the invention, it can be provided that the measuring chamber defines a measuring gap, of a given gap width, on either side of the inner electrode. By the configuration of a narrow measuring gap, a correspondingly high capacitance value can be achieved between the electrodes, by means of which small variations in the temporal characteristic of the electrical permittivity of the liquid can be detected. It can be provided that a sum of the gap widths is smaller than the slot width or the internal clearance of the inlet opening and/or of the discharge opening. It can thus be simply achieved that the liquid flows rapidly in the measuring chamber, as a result of which stationary liquid components, which might invalidate measured values, whether directly or indirectly, can be prevented.

In one configuration of the invention, it can be provided that the inner electrode overlaps the inlet opening on the inner side, in a circumferential direction. A directional change in the liquid flux can thus be compelled upon the admission thereof to the measuring chamber. Effective flushing of the measuring chamber can be achieved accordingly.

Alternatively or additionally, it can be provided that the inner electrode overlaps the discharge opening on the inner side, in a circumferential direction. Thus, alternatively or additionally, a directional change in a flux, for example in the above-mentioned flux, can be compelled upon the discharge thereof from the measuring chamber, which is advantageous for the effective flushing of the measuring chamber.

In one configuration of the invention, it can be provided that the inlet opening constitutes a channel, the channel length of which is greater than a gap width of a measuring gap, for example of the above-mentioned measuring gap, between the outer electrode and the inner electrode. Preferably, the channel is laterally closed, i.e. is delimited by a metal partition which is constituted by the outer electrode or is connected to the latter. As a result, effective shielding between the measuring chamber and an external environment can be achieved.

Alternatively or additionally, it can be provided that the discharge opening constitutes a preferably laterally closed channel, the channel length of which is greater than the or a gap width of a measuring gap, for example of the above-mentioned measuring gap, between the outer electrode and the inner electrode. The discharge opening can thus also be configured for the effective shielding of the measuring chamber. High-frequency capacitance measurements in the measuring chamber can thus be executed with low interference, or even interference-free—for example in the case of the respective constitution of the inlet opening and the discharge opening in the form of a channel, in the manner described.

In one configuration of the invention, it can be provided that the measuring chamber assumes the basic shape of a hollow cylinder. A curved flow path can thus be constituted in the measuring chamber. This has been established as advantageous for the achievement of the continuous and the most comprehensive flushing possible of the measuring chamber. The basic hollow cylindrical shape, which can be supplemented or varied by structural configurations, further effects a double-sided flushing of the inner electrode, which again can be observed as beneficial to the enhancement of measuring accuracy.

In one configuration of the invention, it can be provided that the outer electrode is arranged in an encapsulated housing. The outer electrode can thus be protected from mechanical stresses. Any unwanted electrical contacting of the outer electrode can be prevented accordingly.

In one configuration of the invention, it can be provided that a housing, for example the above-mentioned housing, incorporates an inlet connection corresponding to the inlet opening, and a discharge connection corresponding to the discharge opening. This is advantageous, in that a defined flux characteristic can be achieved. It is further advantageous that the measuring assembly can be easily integrated in a circuit system. It can be provided that the inlet connection and the discharge connection are arranged with a mutual offset in the longitudinal direction. The most comprehensive throughflow possible can thus be achieved in the measuring chamber, in order, for example, to prevent any deposits. Dismantling for cleaning purposes, which is invariably associated with an unwanted calibration operation, can thus be avoided in many cases. A simple configuration of the offset arrangement can be achieved by the discharge connection and the inlet connection being arranged at mutually opposing ends of the measuring chamber. This arrangement can be employed for the prevention of dead spaces, in which stationary liquid components can collect.

In one configuration of the invention, it can be provided that the inlet opening, in the longitudinal direction, extends no further than a region which is encompassed by the inlet connection. Alternatively or additionally, it can also be provided that the discharge opening, in the longitudinal direction, extends no further than a region which is encompassed by the discharge connection. The smallest possible openings can thus be constituted, which do not restrict or impair a flux of liquid. The longitudinal slots can thus be limited to the inlet and discharge region. This has the advantages, that
a) a smaller slot generates a higher signal strength in the measuring system, such that the signal-to-noise (S/N) ratio is improved, i.e. interference is of lower significance,
b) a shorter machining time is required for the milling of slots, thereby reducing production costs.

In one configuration of the invention, it can be provided that the outer electrode is arranged with a clearance to the or a housing. Electrical insulation of the outer electrode can thus be achieved without additional insulation elements.

It is particularly advantageous, if at least one exterior flow baffle is configured on the outer electrode. Thus, an exterior flow of fluid past the outer electrode, in the interspace between the outer electrode and the housing, can be prevented or at least reduced. Alternatively or additionally, it can be provided that at least one recess for a temperature sensor is configured on the outer electrode.

BRIEF DESCRIPTION OF THE DRAWINGS

The invention is described in greater detail hereinafter with reference to an exemplary embodiment, but is not limited to this exemplary embodiment. Further exemplary embodiments proceed from the combination of the features of individual or multiple claims with one another and/or with individual or multiple features of the exemplary embodiment.

In the drawings:

FIG. 5 shows a three-dimensional oblique view of the measuring assembly from FIG. 1, at the section plane represented in FIG. 3, in the direction of the electronics end of the outer electrode, FIG. 6 shows a three-dimensional oblique view of the measuring assembly from FIG. 1, in a longitudinal section analogous to FIG. 2, and FIG. 7 shows the measuring assembly from FIG. 1, in a frontal view of the sectional representation according to FIG. 6.

DETAILED DESCRIPTION

Figure 1:
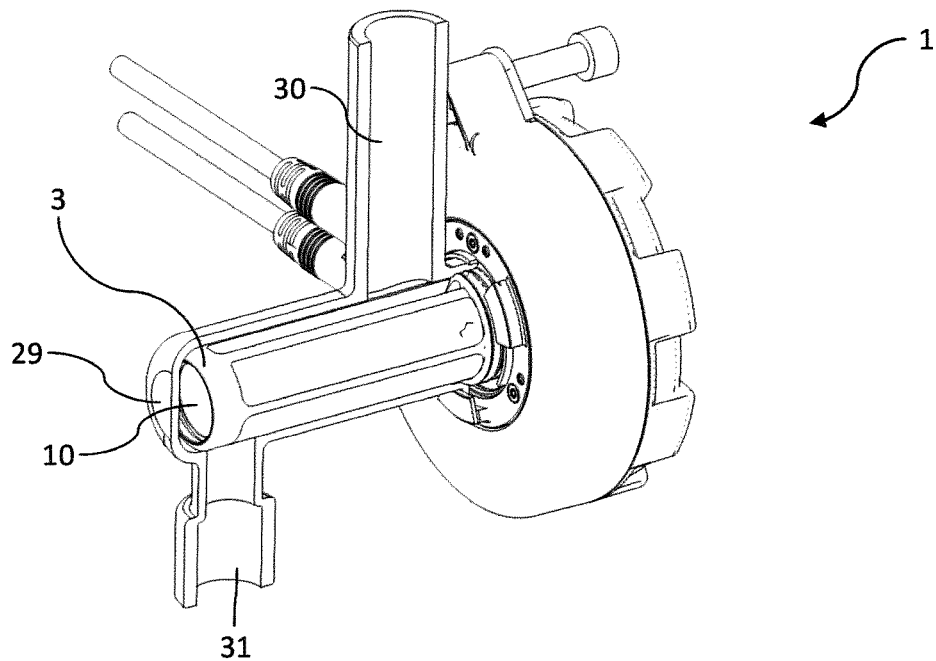
FIG. 1 shows an electrical measuring assembly according to the invention in a three-dimensional oblique view, with a cutaway of the housing in a longitudinal direction.
Figure 2:
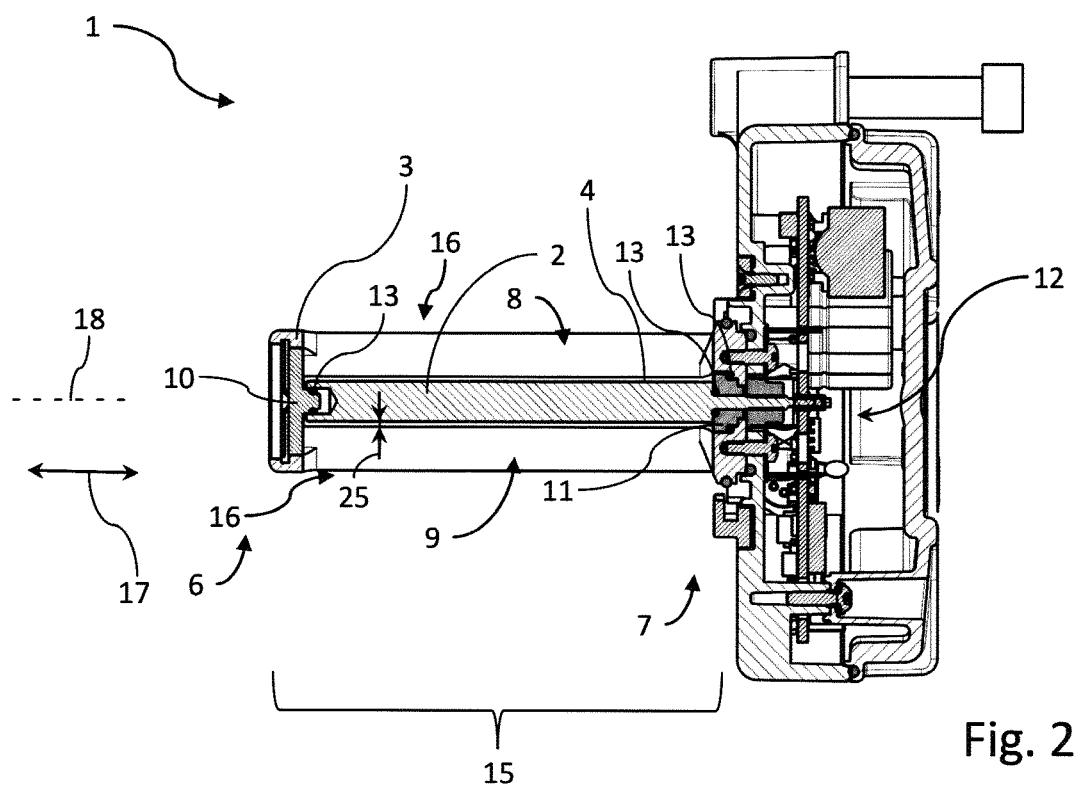
FIG. 2 shows a longitudinal section of the measuring assembly from FIG. 1, with the housing removed.
Figure 3:
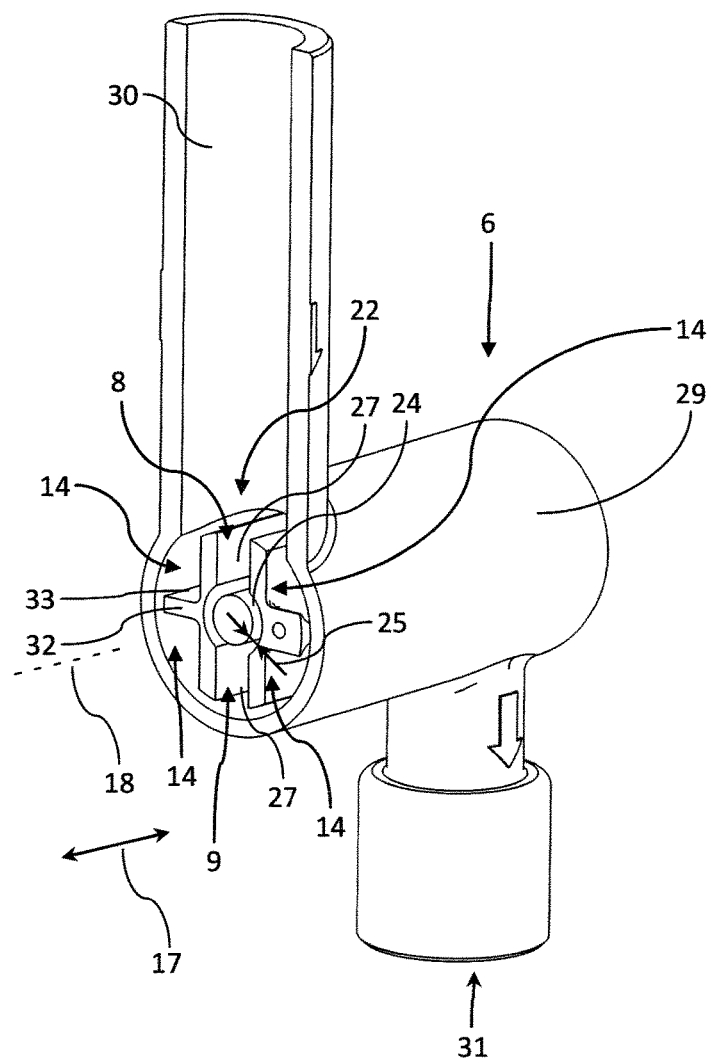
FIG. 3 shows a cross-section of the inlet connection of the measuring assembly from FIG. 1, viewed obliquely in the direction of the free end of the outer electrode.

The figures are described in combination hereinafter.

An electrical measuring assembly 1 is designed in a manner which is known per se for the capacitive measurement of a liquid. To this end, the measuring assembly 1 comprises an inner electrode 2 and an outer electrode 3. The outer electrode 3 encloses the inner electrode 2 to the exterior. The inner electrode 2 is concentrically or coaxially arranged to the outer electrode 3.

A measuring chamber 4 is configured between the inner electrode 2 and the outer electrode 3.

The inner electrode 2 is retained on the outer electrode 3 at axial ends 6, 7 of the measuring chamber 4.

In the outer electrode 3, an inlet opening 8 to the measuring chamber 4 is configured.

On the outer electrode 3, moreover, a discharge opening 9 from the measuring chamber 4 is configured.

The outer electrode 3 and the inner electrode 2 are formed of stainless steel.

The inner electrode 2 is respectively retained at the axial ends 6, 7 by an insulating element 10, 11.

The insulating elements 10, 11 are respectively formed of a chip-machineable glass ceramic.

Both the outer electrode 3 and the inner electrode 2 are formed of food-safe stainless steel. In this case, the steel has a material no. 1.4404 or AISI 316 L, and is identified by the generic name X2CrNiMo 17-12-2.

The glass ceramic of the insulating elements 10, 11 comprises a glass matrix, in this case a borosilicate glass matrix, with glimmer crystals. A composition of 55% fluorophlogopite glimmer and 45% borosilicate glass was selected here. The resulting overall chemical composition is thus 46% silicon oxide, 17% magnesium oxide, 16% aluminum oxide, 10% potassium oxide, 7% boron oxide and 4% fluorine.

This material selection is such that the glass ceramic is essentially pore-free, and can thus absorb no water. In other materials, water absorption is a problem, as the permittivity of the insulating elements 10, 11 is changed as a result. This influences capacitance measurement in an unfavorable manner.

The glass ceramic of the type described has the advantage that, over a wide temperature range, at least between 20° C. and 200° C., permittivity only varies to an insignificant extent, i.e. at most within the measuring accuracy for the capacitance measurement described, or even the measurement of permittivity, and can thus be considered as constant.

At one axial end 6, the measuring assembly 1 is configured in a free-standing arrangement. The other axial end 7 connects to an electronics region 12. The measuring chamber 4 is sealed vis-à-vis this electronics region 12 by means of seals 13.

The insulating elements 10, 11 are respectively formed as round turned parts, and are adjusted to the outer electrode 3 at the axial ends 6, 7 thereof. By this adjustment, a defined centered or central orientation of the inner electrode 2 relative to the outer electrode 3 is achieved, which results in the described coaxial or concentric layout of the electrical measuring assembly 1.

The seals 13 are constituted of food-safe sealing material, for example food-safe rubber or food-safe elastomers. Each of the seals 13 assumes the shape of an O-ring.

From the exterior, material retractions 14 are introduced into the outer electrode 3, which extend over the length 15 of the measuring chamber 4. These material retractions 14 are milled into the material of the outer electrode 3, further to the machine turning thereof.

The material retractions 14 are respectively arranged on either side of the inlet opening 8 and the discharge opening 9.

In the region of the inlet opening 8 and the discharge opening 9, the outer electrode 3 is shaped such that the inlet opening 8 and the discharge opening 9 are respectively configured as a longitudinal slot 16. These longitudinal slots 16 extend in the longitudinal direction 17 of the measuring chamber over the length 15 thereof. In this case, the longitudinal direction 17 coincides with a longitudinal axis 18 of the coaxial arrangement of the electrical measuring assembly 1. In other exemplary embodiments, in place of the longitudinal slots 16, radial bores, for example a row of bores in place of each longitudinal slot 16, are configured.

Figure 4:
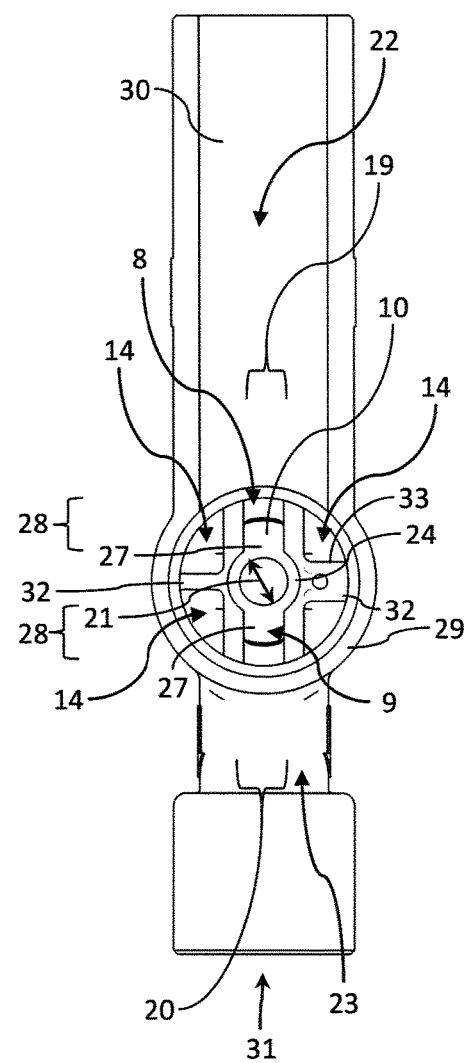
FIG. 4 shows a cross-section according to FIG. 3 of the measuring assembly from FIG. 1, viewed in the longitudinal direction.

In FIG. 4, it can be seen that the internal clearance 19, in this case a slot width, of the longitudinal slots 16 is smaller than an internal diameter 20 of the measuring chamber 4.

The measuring chamber 4 thus constitutes an extension down-circuit of the inlet opening 8 and a taper up-circuit of the discharge opening 9.

The internal clearance 19 is actually selected such that it is smaller than a diameter 21 of the inner electrode 2.

The inner electrode 2 thus constitutes a flow baffle in the connection between the inlet opening 8 and the discharge opening 9, which effects a diversion of the liquid flux.

In relation to the longitudinal axis 18, the inlet opening 8 and the discharge opening 9 are arranged in mutual diametric opposition, such that the inlet opening 8 and the discharge opening 9 open radially outwards on mutually opposing sides of the outer electrode 3.

The inlet opening and the discharge opening 9 are oriented in mutual alignment, wherein the inner electrode 3 is arranged therebetween.

On either side of the inner electrode 2, the annular measuring chamber 4 respectively constitutes, in cross-section, a semicircular or semi-annular measuring gap with a gap width 25.

The gap width 25 of the two measuring gaps 24 is dimensioned such that the sum of the two gap widths 25 is smaller than the internal clearance 19 of the longitudinal slot 16.

By the configuration of the diameter 21 of the inner electrode and the selection of the internal clearance 19 of the longitudinal slots 16, the inner electrode 3 can be arranged such that it overlaps the inlet opening 8 and the discharge opening 9, on the inner side, in the circumferential direction 25.

As a result, a liquid which, for example, is admitted via the inlet opening 8, is entirely diverted into the measuring chamber 4.

From the sectional representations, it can be seen that the measuring chamber 4 assumes the basic shape of a hollow cylinder. A measuring chamber of annular cross-section is formed accordingly.

The inlet opening 8 and the discharge opening 9 respectively constitute a channel 27, which is configured in a laterally closed arrangement along its channel length 28. The channel 27 comprises a metal partition, which is constituted by the outer electrode 3. The channel length 28 is selected such that it is greater than the gap width 25 of each measuring gap 24 and even greater than the sum of these gap widths 25.

This channel 27 executes an external shielding, which substantially prevents any discharge of stray fields from the measuring chamber 4.

The outer electrode 3 is arranged in a housing 29, which is encapsulated vis-à-vis the exterior. The housing 29 thus contains liquid in its housing interior, wherein no liquid exits the latter.

The housing 29 comprises an inlet connection 30 which, in its position and function, corresponds to the inlet opening 8. Liquid admitted via the inlet connection 30 is thus routed to the inlet opening 8.

The housing 29 further comprises a discharge connection 31, which corresponds to the discharge opening 9 in an equivalent manner. Liquid exiting the discharge opening 9 is thus captured in the discharge connection 31 and routed to the exterior.

The inlet connection 30, at one straight end 7, is arranged with an offset in relation to the discharge connection 31 at the other axial end 6. A flux characteristic is thus produced having transverse or radial components, and longitudinal or axial components.

The outer electrode 3 is configured with a clearance to the housing 29, such that electrical insulation vis-à-vis the housing 29 which is also formed of stainless steel is achieved.

It thus proceeds that a given proportion of the liquid flux can also flow outwardly past the outer electrode 3.

In order to maintain this component as small as possible, flow baffles 32 are configured on the exterior of the outer electrode 3, which impair the passage of the liquid flux.

It will be seen that, in the exemplary embodiment, the flow baffles 32 are configured as longitudinal ribs 33, which extend in the longitudinal direction 17 and are respectively arranged between two adjacent material retractions 14.

In one of the longitudinal ribs 33, moreover, a temperature sensor 34 is arranged, by means of which the temperature of an outer electrode 3 is detectable.

This temperature sensor 34 is arranged in a corresponding recess 35 in the form of a blind hole in the longitudinal rib 30.

In the case of an electrical measuring assembly 1, it is thus provided according to the invention that an inner electrode 2 and an outer electrode 3, which form a measuring chamber 4 therebetween for a capacitive examination of a liquid flowing past, are formed from a food-safe stainless steel, wherein the inner electrode 2 is supported at the axial end 6, 7 thereof on the outer electrode 3 by means of insulating elements 10, 11, which are formed from a ceramic or plastic material which is chip-machinable and/or which has a permittivity which is temperature-independent within a working range and/or that is free of pores and/or does not absorb water.

LIST OF REFERENCE NUMBERS

1 Electrical measuring assembly
2 Inner electrode
3 Outer electrode
4 Measuring chamber
6 Axial end
7 Axial end
8 Inlet opening
9 Discharge opening
10 Insulating element
11 Insulating element
12 Electronics region
13 Seal
14 Material retraction
15 Length
16 Longitudinal slot 17 Longitudinal direction
18 Longitudinal axis
19 Internal clearance
20 Internal diameter
21 Diameter
22 Side
23 Side
24 Measuring gap
25 Gap width
27 Channel
28 Channel length
29 Housing
30 Inlet connection
31 Discharge connection
32 Flow baffle
33 Longitudinal ribs
34 Temperature sensor
35 Recess

The invention claimed is:

1. An electrical measuring assembly (1) for capacitive measurement of a liquid, the electrical measuring assembly comprising:
an outer electrode (3),
an inner electrode (2) arranged concentrically to the outer electrode (3), such that the outer electrode encloses the inner electrode forming a measuring chamber (4) between the inner electrode (2) and the outer electrode (3),
the inner electrode (2) is secured to the outer electrode (3) at axial ends of the measuring chamber (4),
at least one inlet opening (8) to the measuring chamber (4) and at least one discharge opening (9) from the measuring chamber (4) are provided in the outer electrode (3),
the outer electrode (3) and the inner electrode (2) are formed of stainless steel, and
insulating elements (10, 11) that retain the inner electrode (2) at the axial ends (6, 7), the insulating elements (10, 11) are formed of a food-safe material, comprising a glass ceramic or a plastic, that is at least one of
a) a material having a permittivity that, over a temperature range from 20° C. to 200° C., varies by a maximum of 30%,
b) a pore-free material,
c) a material which absorbs no water, or
d) a chip-machineable material.

2. The electrical measuring assembly (1) as claimed in claim 1, wherein the stainless steel is food-safe, and comprises at least one of material number 1.4404, AISI 316L, or X2CrNiMo17-12-2.

3. The electrical measuring assembly (1) as claimed in claim 1, wherein the insulating elements (10, 11) comprise a glass matrix, with glimmer crystals, including 55% fluorophlogopite glimmer and/or 45% borosilicate glass, wherein a chemical composition of 46% silicon oxide, 17% magnesium oxide, 16% aluminum oxide, 10% potassium oxide, 7% boron oxide and 4% fluorine.

4. The electrical measuring assembly (1) as claimed in claim 1, wherein the insulating elements (10, 11) are turned parts.

5. The electrical measuring assembly (1) as claimed in claim 1, further comprising at least one seal (13) of a food-safe sealing material arranged between the inner electrode (2) and at least one of the insulating elements (10, 11), or between at least one of the insulating elements (10, 11) and the outer electrode (3), or both.

6. The electrical measuring assembly as claimed in claim 1, wherein the outer electrode (3), on an outer side thereof, incorporates at least one material retraction (14), at least one of adjacent to at least one of the inlet opening (8) or the discharge opening (9) or over a length of the measuring chamber (4).

7. An electrical measuring assembly (1) for capacitive measurement of a liquid, the electrical measuring assembly comprising:
an outer electrode (3),
an inner electrode (2) arranged concentrically to the outer electrode (3), such that the outer electrode encloses the inner electrode forming a measuring chamber (4) between the inner electrode (2) and the outer electrode (3),
the inner electrode (2) is secured to the outer electrode (3) at axial ends of the measuring chamber (4),
at least one inlet opening (8) to the measuring chamber (4) and at least one discharge opening (9) from the measuring chamber (4) are provided in the outer electrode (3),
the inlet opening (8) and the discharge opening (9) are respectively configured as radially open, and an internal clearance (19) of the inlet opening (8) and the discharge opening (9), transversely to a longitudinal direction (17), is smaller than an internal diameter (20) of the measuring chamber (4).

8. The electrical measuring assembly (1) as claimed in claim 7, wherein the inlet opening (8) and the discharge opening (9) are respectively configured as a radially open longitudinal slot (16), respectively oriented in a longitudinal direction (17) of the outer electrode (3), and the internal clearance (19) comprises a slot width, or at least one of the inlet opening (8) or the discharge opening (9) is configured as at least one bore.

9. The electrical measuring assembly (1) as claimed in claim 7, wherein at least one of the inlet opening (8) or the discharge opening (9) extends over at least half of a length of the measuring chamber (4).

10. The electrical measuring assembly (1) as claimed in claim 7, wherein the inlet opening (8) and the discharge opening (9) are arranged on mutually opposing sides (22, 23) of the outer electrode (3), and the inner electrode (2) is arranged between the inlet opening (8) and the discharge opening (9).

11. The electrical measuring assembly (1) as claimed in claim 7, wherein the measuring chamber (4) defines a measuring gap (24), having a gap width (25), on either side of the inner electrode (2), and a sum of the gap widths (25) is smaller than the internal clearance (19) of at least one of the inlet opening (8) or of the discharge opening (9).

12. The electrical measuring assembly (1) as claimed in claim 7, wherein the inner electrode (2) overlaps at least one of the inlet opening (8) or the discharge opening (9) on an inner side, in a circumferential direction.

13. The electrical measuring assembly (1) as claimed in claim 11, wherein at least one of one of the inlet opening (8) or the discharge opening (9) comprises a channel (27), a channel length (28) of which is greater than the gap width (25) of the measuring gap (24) between the outer electrode (3) and the inner electrode (2).

14. The electrical measuring assembly (1) as claimed in claim 7, wherein the measuring chamber (4) has a hollow cylinder shape.

15. The electrical measuring assembly as claimed in claim 7, wherein the outer electrode (3) is arranged in an encapsulated housing (29).

16. The electrical measuring assembly (1) as claimed in claim 15, wherein the housing incorporates an inlet connection (30) corresponding to the inlet opening (8), and a discharge connection (31) corresponding to the discharge opening (9), and the inlet connection (30) and the discharge connection (31) are arranged with a mutual offset in the longitudinal direction.

17. The electrical measuring assembly (1) as claimed in claim 16, wherein the inlet opening (8), in the longitudinal direction (17), extends no further than a region which is encompassed by the inlet connection (30) or the discharge opening (9), in the longitudinal direction (17), extends no further than a region which is encompassed by the discharge connection (30), or both.

18. The electrical measuring assembly (1) as claimed in claim 16, wherein the outer electrode (3) is arranged with a clearance to the housing, and at least one of an exterior flow baffle (32) is configured on the outer electrode (3) or at least one recess (35) is configured on the outer electrode for a temperature sensor (34).

19. The electrical measuring assembly (1) as claimed in claim 7, further comprising:
   the outer electrode (3) and the inner electrode (2) are formed of stainless steel, and
   insulating elements (10, 11) that retain the inner electrode (2) at the axial ends (6, 7), the insulating elements (10, 11) are formed of a food-safe material, comprising a glass ceramic or a plastic, that is at least one of
   a) a material having a permittivity that, over a temperature range from 20° C. to 200° C., varies by a maximum of 30%,
   b) a pore-free material,
   c) a material which absorbs no water, or
   d) a chip-machineable material.

\* \* \* \* \*